United States Patent [19]

Torii et al.

[11] Patent Number: 5,196,530
[45] Date of Patent: Mar. 23, 1993

[54] PROCESS FOR PREPARING 2-EXO-METHYLENEPENAM DERIVATIVES

[75] Inventors: Sigeru Torii; Hideo Tanaka, both of Okayama; Masatoshi Taniguchi, Osaka; Michio Sasaoka, Tokushima; Takashi Shiroi, Tokushima; Yutaka Kameyama, Tokushima, all of Japan

[73] Assignee: Otsuka Kagaku Kabushiki Kaisha, Osaka, Japan

[21] Appl. No.: 848,939

[22] Filed: Mar. 10, 1992

[30] Foreign Application Priority Data

Mar. 11, 1991 [JP] Japan ...................................... 3-72449

[51] Int. Cl.⁵ ............................................ C07D 499/00
[52] U.S. Cl. .................................................... 540/310
[58] Field of Search ................. 540/310; 514/210, 192, 514/195

[56] References Cited

U.S. PATENT DOCUMENTS 4,496,484  1/1985  Micetich et al. ..................... 540/310

*Primary Examiner*—Nicholas S. Rizzo
*Attorney, Agent, or Firm*—Armstrong, Westerman, Hattori, McLeland & Naughton

[57] ABSTRACT

The present invention provides a process for preparing a 2-exo-methylenepenam derivative represented by the formula (2), the process being characterized by reacting an allenyl β-lactam compound represented by the formula (1) with a metallic reducing agent, in which $R^1$, $R^2$, $R^3$ and X are defined in the specification.

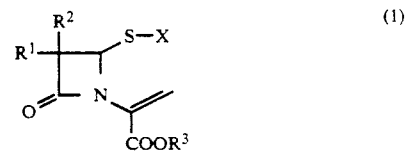

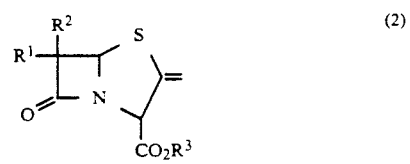

3 Claims, No Drawings

PROCESS FOR PREPARING 2-EXO-METHYLENEPENAM DERIVATIVES

The present invention relates to a novel process for preparing 2-exo-methylenepenam derivatives.

The compounds heretofore known among the 2-exo-methylenepenam derivatives represented by the formula (2)

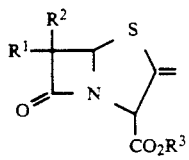

(2)

wherein $R^1$ is a hydrogen atom, halogen atom, amino or protected amino, $R^2$ is a hydrogen atom, halogen atom, lower alkoxyl, lower acyl, lower alkyl, lower alkyl substituted with hydroxyl or protected hydroxyl, hydroxyl or protected hydroxyl, $R^1$ and $R^2$ representing $=O$ when taken together, $R^3$ is a hydrogen atom or carboxylic acid protecting group are only those wherein $R^1$ is amino or protected amino, and $R^2$ is a hydrogen atom. The process disclosed in J. Chem. Soc., Chem. Commun., 81 (1987) is also the only process known for preparing these derivatives. However, this process is low in yield, includes reaction steps which necessitate cumbersome reaction procedures or separation procedures, and is in no way satisfactory as a practically useful process.

An object of the present invention is to provide an industially advantageous process for preparing the 2-exo-methylenepenam derivative in a high yield with high purity by a safe and easy procedure free of the drawback of the conventional process.

The above and other objects of the invention will become apparent from the following description.

The present invention provides a process for preparing a 2-exo-methylenepenam derivative represented by the formula (2), the process being characterized by reacting an allenyl β-lactam compound represented by the formula (1)

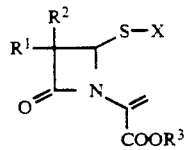

(1)

wherein $R^1$ is a hydrogen atom, halogen atom, amino or protected amino, $R^2$ is a hydrogen atom, halogen atom, lower alkoxyl, lower acyl, lower alkyl, lower alkyl substituted with hydroxyl or protected hydroxyl, hydroxyl or protected hydroxyl, $R^1$ and $R^2$ representing $=O$ when taken together, $R^3$ is a hydrogen atom or carboxylic acid protecting group, and X is the group $-SO_2R^4$ or the group $-SR^4$, $R^4$ being substituted or unsubstituted aryl or substituted or unsubstituted nitrogen-containing aromatic heterocyclic group with a metallic reducing agent.

The allenyl β-lactam derivative represented by the formula (1) and to be used as the starting material in the present invention is a novel compound which has not been disclosed in literature, and can be prepared, for example, by reacting an azetidinone derivative represented by the formula (3) given below with a base.

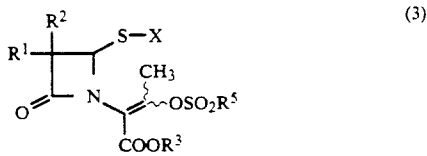

(3)

wherein $R^1$, $R^2$, $R^3$ and X are as defined above, and $R^5$ is substituted or unsubstituted lower alkyl or substituted or unsubstituted aryl.

Examples of groups mentioned herein are as follows. The term "halogen atom" as used hereinafter means, for example, fluorine, chlorine, bromine or iodine atom unless otherwise specified. The term "lower alkyl" means a straight-chain or branched $C_{1-4}$ alkyl group such as methyl, ethyl, n-propyl, isopropyl, n-butyl, isobutyl, sec-butyl or tert-butyl. The term "aryl" means, for example, phenyl, naphthyl or the like.

Exemplary of the protected amino represented by $R^1$ are phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-tert-butylbenzamido, p-methoxybenzamido, p-chlorobenzamido and p-bromobenzamido groups, the groups disclosed in Theodora W. Greene, "Protective Groups in Organic Synthesis" (hereinafter referred to merely as the "literature"), Chap. 7 (pp. 218~287), phenylglycylamido group, phenylglycylamido groups having protected amino, p-hydroxyphenylglycylamido group, and p-hydroxyphenylglycylamido groups having protected amino and/or protected hydroxyl. Examples of protective groups for amino are those disclosed in the literature, Chap. 7 (pp. 218~287). Examples of protective groups for the hydroxyl of p-hydroxyphenylglycylamido group are those disclosed in the literature, Chap. 2 (pp. 10~72).

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl.

Exemplary of the carboxylic acid protecting group represented by $R^3$ are benzyl, p-methoxybenzyl, p-nitrobenzyl, diphenylmethyl, trichloroethyl, tert-butyl, and those disclosed in the literature, Chap. 5 (pp. 152–192).

While $R^4$ represents a nitrogen-containing aromatic heterocyclic group which may have a substituent or substituents, exemplary of the nitrogen-containing aromatic hetrocyclic group are thiazol-2-yl, thiadiazol-2-yl, benzothiazol-2-yl, oxazol-2-yl, benzoxazol-2-yl, imidazol-2-yl, benzoimidazol-2-yl, pyrimidinyl, pyridyl and the like.

Exemplary of the substituent which may be substituted in the aryl or nitrogen-containing aromatic heterocyclic group represented by $R^4$ are halogen atoms, hydroxyl, nitro, cyano, aryl, lower alkyl, amino, mono lower alkylamino, di lower alkylamino, mercapto, alkylthio or arylthio represented by the group $R^6S-$ (wherein $R^6$ is lower alkyl or aryl), formyloxy, acyloxy represented by the group $R^6COO-$ (wherein $R^6$ is as defined above), formyl, acyl represented by the group $R^6CO-$ (wherein $R^6$ is as defined above), alkoxyl or aryloxy represented by $R^6O-$ (wherein $R^6$ is as defined above), carboxyl, alkoxycarbonyl or aryloxycarbonyl represented by the group $R^6OCO-$ (wherein $R^6$ is as defined above), etc. The aryl or nitrogen-containing aromatic heterocyclic group represented by $R^4$ may have one or at least two same or different groups selected from among the above substituents.

$R^5$ represents lower alkyl or aryl which may have a substituent or substituents, examples of which are those mentioned for $R^4$. The lower alkyl or aryl represented by $R^5$ may have one or at least two same or different groups selected from among the foregoing substituents. Such substituent(s) may be positioned on at least one carbon atom of the alkyl or aryl.

To prepare the allenyl $\beta$-lactam compound of the formula (1) to be used as a starting material according to the invention, the azetidinone derivative of the formula (3) is reacted with a base in a suitable solvent. The base to be used is preferably an aliphatic or aromatic amine. Examples of such amines are triethylamine, diisopropylamine, ethyldiisopropylamine, tributylamine, DBN(1,5-diazabicyclo[3.4.0]nonene-5), DBU(1,8-diazabicyclo[5.4.0]undecene-7), DABCO(1,4-diazabicyclo[2.2.2]octane), piperidine, N-methylpiperidine, 2,2,6,6-tetramethylpiperidine, morpholine, N-methylmorpholine, N,N-dimethylaniline, N,N-dimethylaminopyridine and the like.

The base is used usually in an amount of 1 to 12 moles, preferably 1 to 6 moles, per mole of the compound of the formula (3). The solvent to be used can be any of a wide variety of those which dissolve the compound of the formula (3) and which are inert under the reaction condition employed. Examples of useful solvents are lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ethers such as diethyl ether, ethyl propyl ether, ethyl butyl ether, dipropyl ether, diisopropyl ether, dibutyl ether, methyl cellosolve and dimethoxyethane; cyclic ethers sush as tetrahydrofuran and dioxane; nitriles such as acetonitrile, propionitrile, butyronitrile, isobutyronitrile and valeronitrile; substituted or unsubstituted aromatic hydrocarbons such as benzene, toluene, xylene, chlorobenzene and anisole; hydrocarbon halides such as dichloromethane, chloroform, dichloroethane, trichloroethane, dibromoethane, propylene dichloride, carbon tetrachloride and Freons; hydrocarbons such as pentane, hexane, heptane and octane; cycloalkanes such as cyclopentane, cyclohexane, cycloheptane and cyclooctane; amides such as dimethylformamide and dimethylacetamide; dimethyl sulfoxide; etc. These solvents are used singly or in admixture. The solvent may contain water. The solvent is used preferably in an amount of about 0.5 to about 200 liters, more preferably about 1 to about 50 liters, per kg of the compound of the formula (3). The reaction is conducted at $-70°$ C. to 100° C., preferably $-50°$ C. to 50° C.

According to the present invention, the allenyl $\beta$-lactam compound represented by the formula (1) and prepared from the compound of the formula (3) by the foregoing process is isolated by extraction or like usual method and thereafter reacted as it is with a metallic reducing agent without necessitating any special purifying procedure, whereby the compound (1) can be converted to a 2-exo-methylenepenam derivative represented by the formula (2).

The above reaction is conducted usually in a solvent. The solvent to be used can be any of a wide variety of those known in the art which dissolve the compound of the formula (1) and which are inert under the reaction condition employed. Examples of useful solvents are alcohols such as methanol, ethanol, propanol, isopropanol, butanol and tertbutanol; lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ketones such as acetone, methyl ethyl ketone, methyl isopropyl ketone, methyl butyl ketone, methyl isobutyl ketone and diethyl ketone; ethers such as diethyl ether, ethyl propyl ether, ethyl butyl ether, dipropyl ether, diisopropyl ether, dibutyl ether, methyl cellosolve and dimethoxyethane; cyclic ethers such as tetrahydrofuran and dioxane; nitriles such as acetonitrile, propionitrile, butyronitrile, isobutyronitrile and valeronitrile; substituted or unsubstituted aromatic hydrocarbons such as benzene, toluene, xylene, chlorobenzene and anisole; hydrocarbon halides such as dichloromethane, chloroform, dichloroethane, trichloroethane, dibromoethane, propylene dichloride, carbon tetrachloride and Freons; hydrocarbons such as pentane, hexane, heptane and octane; cycloalkanes such as cyclopentane, cyclohexane, cycloheptane and cyclooctane; amides such as dimethylformamide and dimethylacetamide; dimethyl sulfoxide; etc. These solvents are used singly or in admixture. The solvent may contain water. The solvent is used preferably in an amount of about 0.5 to about 200 liters, more preferably about 1 to about 50 liters, per kg of the compound of the formula (1).

Examples of metallic reducing agent for use in the above reaction are metallic lead, metallic titanium, metallic zirconium, metallic gallium, metallic bismuth, metallic antimony, etc. The metal to be reacted is not specifically limited in shape but can be used in any of various forms such as powder, plate, block and wire forms. However, to complete the reaction at a lower temperature within a shorter period of time, the metal is preferably in the form of a powder. When the metallic reducing agent is powdery, the particle size thereof can be determined from a wide range. Preferably, however, the agent is about 10 to 500 mesh in particle size. The metallic reducing agent is used in an amount of about 1 to about 10 mole atom, preferably about 1 to about 4 mole atom per mole of the compound of the formula (1).

According to the present invention, presence of a metal, which is greater than the metallic reducing agent in ionization tendency, in the reaction system makes it possible to greatly reduce the amount of metallic reducing agent to be used, facilitate the treatment to be conducted after the reaction and carry out the reaction at a lower temperature within a shorter length of time. Examples of combinations of the metallic reducing agent and a metal greater than the agent in ionization tendency are Pb/Al, Bi/Al, Ti/Zn, Ga/Zn, Zr/Zn, Sb/Zn, Te/Zn, Pb/Zn, Bi/Zn, Bi/Mg, Bi/Sn, Sb/Sn, etc. These metals can be used singly, or at least two of them are usable in combination. The metal to be used is not limited specifically in shape but can be in any of various forms such as powder, plate, foil, block and wire form. To permit the reaction to proceed more smoothly, it is advantageous to use the metal in the form of a powder. Although the particle size of powdery metals can be determined from a wide range, it is preferably about 10 to about 300 mesh. The metal is used in an amount usually of about 1 to about 50 mole atom, preferably about 1 to about 10 mole atom per mole of the compound of the formula (1).

When such a metal which is greater than the metallic reducing agent in ionization tendency is to be used, it is more preferable to use a compound of the particular metal in place of the metallic reducing agent.

Examples of useful metal compounds are lead halide such as lead fluoride, lead chloride, lead bromide and lead iodide; inorganic acid salts of lead such as lead nitrate, lead sulfate, lead perchlorate, lead borate, lead carbonate and lead phosphate; fatty acid salts of lead such as lead acetate, lead oxalate and lead stearate; lead oxide; lead hydroxide; titanium halides such as titanium fluoride, titanium chloride, titanium bromide and titanium iodide; inorganic acid salts of titanium such as titanium sulfate and titanium nitrate; gallium halides such as gallium fluoride, gallium chloride, gallium bromide and gallium iodide; inorganic acid salts of gallium such as gallium sulfate, gallium nitrate and gallium perchlorate; zirconium halides such as zirconium fluoride, zirconium chloride, zirconium bromide and zirconium iodide; zirconium sulfate; tellurium halides such as tellurium bromide, tellurium chloride and tellurium iodide; bismuth halides such as bismuth fluoride, bismuth chloride, bismuth bromide and bismuth iodide; inorganic acid salts of bismuth such as bismuth nitrate and bismuth sulfate; bismuth oxide; antimony halides such as antimony fluoride, antimony chloride, antimony bromide and antimony iodide; inorganic acid salts of antimony such as antimony sulfate; antimony oxide; etc. Theoretically, a satisfactory result will be achieved if one molecular of such a metal compound is present in the reaction system, whereas it is generally desirable to use about 0.0001 to about 2.0 moles of the compound per mole of the compound of the formula (1).

Although the reaction temperature varies with the material and solvent to be used and can not be determined specifically, it is usually about −20° to about 100° C., preferably about 0° to about 50° C. When conducted with ultrasonic irradiation, the reaction is likely to proceed at a higher velocity.

The desired 2-exo-methylenepenam derivative of the formula (2) can be isolated from the reaction mixture in the form of a substantially pure product, for example, by subjecting the mixture to extraction in the usual manner. When required, the product is further purified by a conventional method of purification such as recrystallization or column chromatography.

The desired 2-exo-methylenepenam derivative of the formula (2) can be prepared in a high yield with high purity by the process of the invention which is industrially advantageous and easy to practice.

The invention will be described in greater detail with reference to the following examples. Incidentally, Ph stands for phenyl.

REFERENCE EXAMPLE 1

Compound of the formula (4)→compound of formula (5)

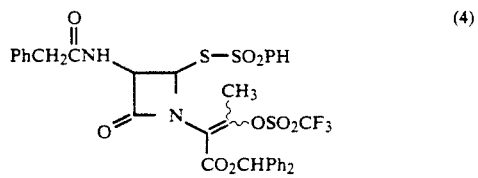

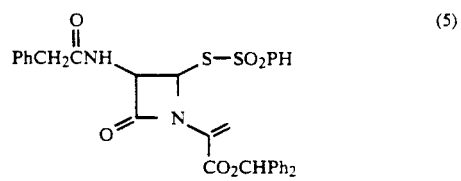

One gram of the compound of the formula (4) ($R^1$=phenylacetamido, $R^2$=H, $R^3$=diphenylmethyl, X=phenylsulfonyl, $R^5$=trifluoromethyl) was dissolved in 10 ml of N,N-dimethylformamide. After cooling the solution to −30° C., 0.43 ml of triethylamine was added to the solution, followed by stirring at −30° C. for 1 hour for reaction. The reaction mixture was extracted with ethyl acetate, and the extract was washed with water and then dried over anhydrous sodium sulfate. Concentration of the dried extract gave the compound of the formula (5) ($R^1$, $R^2$, $R^3$ and X are the same as above) in a yield of 99%.

NMR (CDCl$_3$); δ ppm: 3.61 (s, 2H), 5.31 (dd, 1H, J=5 Hz, and 7 Hz), 5.57 and 5.70 (ABq, 2H, J=15 Hz), 5.84 (d, 1H, J=5 Hz), 6.02 (d, 1H, J=7 Hz), 6.81 (s, 1H), 7.22~7.73 (m, 20H).

REFERENCE EXAMPLES 2 TO 8

The following compounds (5) to (8) were each prepared from starting compound listed in Table 1 by the same reaction as in Example 1.

TABLE 1

| Ref. Ex. | Compound (formula 3) | | | | | Compound (formula 1) | |
|---|---|---|---|---|---|---|---|
| | $R^1$ | $R^2$ | $R^3$ | X | $R^5$ | yield | (%) |
| 2 | PhCH$_2$CONH | H | CHPh$_2$ | SO$_2$Ph | 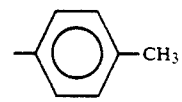 | (5) | 100 |

TABLE 1-continued

| Ref. Ex. | Compound (formula 3) | | | | | Compound (formula 1) | |
|---|---|---|---|---|---|---|---|
| | $R^1$ | $R^2$ | $R^3$ | X | $R^5$ | yield | (%) |
| 3 | PhCH$_2$CONH | H | CH$_2$–C$_6$H$_4$–OCH$_3$ | SO$_2$Ph | CF$_3$ | (6) | 99 |
| 4 | PhCH$_2$CONH | H | CH$_2$–C$_6$H$_4$–OCH$_3$ | SO$_2$Ph | CH$_3$ | (6) | 86 |
| 5 | PhCH$_2$CONH | H | CH$_3$ | SO$_2$Ph | CF$_3$ | (7) | 100 |
| 6 | PhCH$_2$CONH | H | CHPh$_2$ | benzothiazol-2-yl-S– | CF$_3$ | (8) | 99 |
| 7 | H | H | CH$_2$–C$_6$H$_4$–OCH$_3$ | SO$_2$Ph | CF$_3$ | (9) | 99 |
| 8 | H | H | CHPh$_2$ | SO$_2$Ph | CF$_3$ | (10) | 99 |

NMR data as to the compounds (6) to (10) is collectively given below.

Compound (6): 3.58 (s, 2H), 3.80 (s, 3H), 5.10 (s, 2H), 5.32 (dd, 1H, J=5 Hz and 8 Hz), 5.60 and 5.47 (ABq, 2H, J=15 Hz), 5.87 (d, 1H, J=5 Hz), 6.08 (d, 1H, J=8 Hz), 6.85~7.83 (m, 14H).

Compound (7): 3.59 (s, 2H), 3.74 (s, 3H), 5.33 (dd, 1H, J=5 Hz and 8 Hz), 5.54 and 5.64 (ABq, 2H, J=15 Hz), 5.88 (d, 1H, J=5 Hz), 6.02 (d, 1H, 8 Hz), 7.20~7.90 (m, 10H).

Compound (8): 3.67 (s, 2H), 5.25 (dd, 1H, J=5 Hz and 8 Hz), 5.69 (d, 1H, J=5 Hz), 5.60 and 5.76 (ABq, 2H, J=15 Hz), 6.71 (s, 1H), 7.00~7.34 (m, 20H).

Compound (9); 3.02 (dd, 1H, J=2.6 Hz and 15.7 Hz), 3.58 (dd, 1H, J=5.4 Hz and 15.7 Hz), 3.79 (s, 3H), 5.17 (s, 2H), 5.47 and 5.60 (ABq, 2H, J=15.2 Hz), 5.62 (dd, 1H, J=2.6 Hz and 5.4 Hz), 6.87~7.89 (m, 9H).

Compound (10); 2.99 (dd, 1H, J=2.6 Hz and 15.7 Hz), 3.53 (dd, 1H, J=5.5 Hz and 15.7 Hz), 5.56 (dd, 1H, J=2.6 Hz and 5.5 Hz), 5.54 and 5.66 (ABq, 2H, J=15.2 Hz), 6.88 (s, 1H), 7.29~7.76 (m, 15H).

REFERENCE EXAMPLES 9 to 11

The compound of the formula (5) was obtained in the yield shown in Table 2 by the same reaction as in Example 1 with the exception of changing the solvent and temperature for the reaction as listed in Table 2.

TABLE 2

| Ref. Ex. | solvent | temperature | yield (%) |
|---|---|---|---|
| 9 | tetrahydrofuran | −20° C. | 99 |
| 10 | tetrahydrofuran | 20° C. | 98 |
| 11 | methylene chloride | −20° C. | 95 |

EXAMPLE 1

Compound of formula (6)→compound of formula (11)

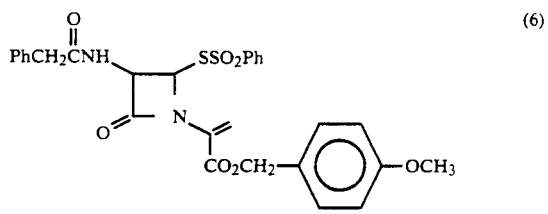
(6)

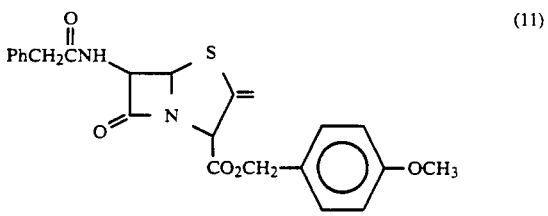
(11)

A 100 mg quantity of the compound of the formula (6) ($R^1$=phenylacetamido, $R^2$=H, $R^3$=p-methoxybenzyl, X=phenylsulfonyl) was dissolved in 1 ml of N,N-dimethylformamide, followed by the addition of 50 mg of zinc powder and then 50 mg of BiCl$_3$ to the solution. The mixture was reacted at room temperature for 30 minutes with stirring To the reaction mixture thus obtained was added 1N hydrochloric acid, followed by extraction with ethyl acetate. The resulting organic layer was separated off, washed with water, dried over anhydrous magnesium sulfate and concentrated in a vacuum. The residue obtained was purified by silica gel column chromatography, giving the compound of the formula (11) ($R^1$=phenylacetamido, $R^2$=H, $R^3$=p-methoxybenzyl) in a yield of 92%.

NMR (CDCl$_3$); δ ppm: 3.61 (ABq, 2H, J=16 Hz), 3.80 (s, 3H), 5.11 (s, 2H), 5.18 (t, 1H, J=1 Hz), 5.24 (t, 1H, J=1 Hz), 5.35 (t, 1H, J=1 Hz), 5.57 (d, 1H, J=4 Hz), 5.75 (dd, 1H, J=4 Hz and 9 Hz), 6.07 (d, 1H, J=9 Hz), 6.85~7.40 (m, 9H).

EXAMPLE 2

Compound of formula (5)→compound of formula (12)

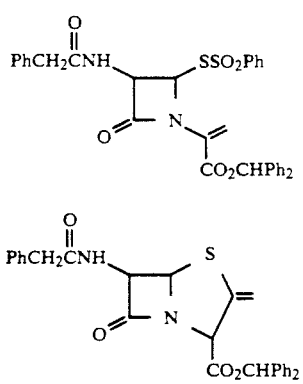

The same reaction as in Example 1 was conducted using 200 mg of the compound of the formula (5) ($R^1$=phenylacetamido, $R^2$=H, $R^3$=diphenylmethyl, X=phenylsulfonyl) as the starting material to obtain the compound of the formula (12) ($R^1$=phenylacetamido, $R^2$=H, $R^3$=diphenylmethyl) in a yield of 89%.

NMR (CDCl$_3$); δ ppm: 3.62 (s, 2H), 5.26~5.28 (m, 2H), 5.37 (t, 1H, J=2 Hz), 5.61 (d, 1H, J=4 Hz), 5.76 (dd, 1H, J=4 Hz) and 9 Hz), 6.14 (d, 1H, J=9 Hz), 6.82 (s, 1H), 7.20~7.41 (m, 15H).

EXAMPLE 3

Compound of formula (7)→compound of formula (13)

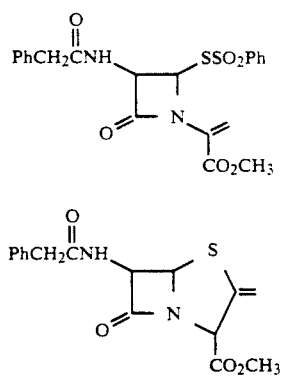

A 50 mg quantity of the compound of the formula (7) ($R^1$=phenylacetamido, $R^2$=H, $R^3$=methyl, X=phenylsulfonyl) was dissolved in 0.5 ml of N,N-dimethylformamide. To the solution were added 50 mg of zinc powder and 10 μl of TiCl$_4$, and the mixture was stirred at room temperature for 25 minutes for reaction. The reaction mixture was thereafter treated in the same manner as in Example 1, giving the compound of the formula (13) ($R^1$=phenylacetamido, $R^2$=H, $R^3$=methyl) in a yield of 95%.

NMR (CDCl$_3$); δ ppm: 3.62 (ABq, 2H, J=16 Hz), 3.78 (s, 3H), 5.19 (t, 1H, J=2 Hz), 5.28 (t, 1H, J=2 Hz), 5.40 (t, 1H, J=2 Hz), 5.60 (d, 1H, J=4 Hz), 5.77 (dd, 1H, J=4 Hz and 9 Hz), 6.20 (d, 1H, J=9 Hz), 7.27~7.39 (m, 5H)

EXAMPLE 4

Compound of formula (9)→compound of formula (14)

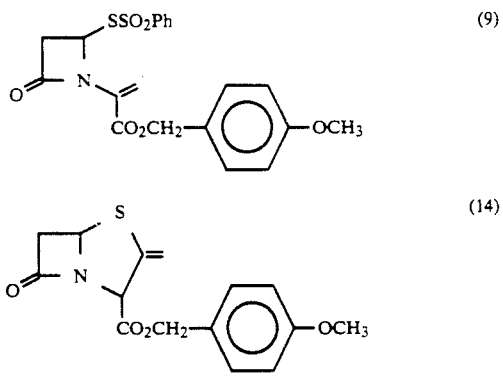

The same reaction as in Example 1 was conducted using 189 mg of the compound of the formula (9) ($R^1=R^2$=H, $R^3$=p-methoxybenzyl, X=phenylsulfonyl) as the starting material to obtain the compound of the formula (14) ($R^1=R^2$=H, $R^3$=p-methoxybenzyl) in a yield of 88%.

NMR (CDCl$_3$); δ ppm: 3.16 (dd, 1H, J=1.5 Hz and 16 Hz), 3.66 (dd, 1H, J=4 Hz and 16 Hz), 3.82 (s, 3H), 5.13 (s, 2H), 5.24 (dd, 1H, J=1.8 Hz and 1.8 Hz), 5.28 (dd, 1H, J=1.8 Hz and 1.8 Hz), 5.32 (dd, 1H, J=1.8 Hz and 1.8 Hz), 5.38 (dd, 1H, J=1.5 Hz and 4 Hz), 6.87~7.30 (m, 4H).

EXAMPLE 5

Compound of formula (10)→compound of formula (15)

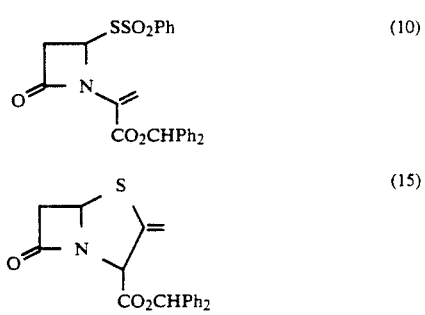

The same reaction as in Example 1 was conducted using 720 mg of the compound of the formula (10) ($R^1=R^2$=H, $R^3$=diphenylmethyl, X=phenylsulfonyl) as the starting material to obtain the compound of the formula (15) ($R^1=R^2$=H, $R^3$=diphenylmethyl) in a yield of 86%.

NMR (CDCl$_3$); δ ppm; 3.12 (dd, 1H, J=1.5 Hz and 16 Hz), 3.60 (dd, 1H, J=4.1 Hz and 16 Hz), 5.23 (dd, 1H, J=1.8 Hz and 1.8 Hz), 5.32 (dd, 1H, J=1.8 Hz and 1.8 Hz), 5.36 (dd, 1H, J=1.5 Hz and 4.1 Hz), 5.37 (dd, 1H, J=1.8 Hz and 1.8 Hz), 6.87 (s, 1H), 7.27~7.35 (m, 10H)

EXAMPLES 6 TO 11

The compound of the formula (11) ($R^1$=phenylacetamido, $R^2$=H, $R^3$=p-methoxybenzyl) was obtained by conducting the same reaction as in Example 1 with the exception of changing the metal and the metal salt. Table 3 shows the result.

TABLE 3

| Ex. | metal salt | metal | time (min) | yield (%) |
|---|---|---|---|---|
| 6 | PbBr$_2$ | Al | 14 | 89 |
| 7 | GaCl$_3$ | Zn | 30 | 70 |
| 8 | SbCl$_3$ | Zn | 30 | 72 |
| 9 | ZrCl$_3$ | Zn | 60 | 82 |
| 10 | TeCl$_4$ | Zn | 60 | 83 |
| 11 | TiCl$_4$ | Zn | 30 | 85 |

We claim:

1. A process for preparing a 2-exo-methylenepenam of the formula

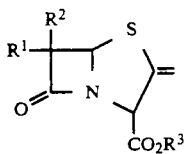

wherein $R^1$ is hydrogen, halogen, amino or protected amino; $R^2$ is hydrogen, halogen, lower alkoxyl, lower acyl, lower alkyl, lower alkyl substituted with hydroxyl or protected hydroxyl, hydroxyl or protected hydroxyl; $R^1$ and $R^2$ taken together represent =O; and $R^3$ is hydrogen or a carboxylic acid protecting group; which comprises cyclizing an allenyl-β-lactam of the formula

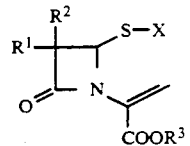

wherein $R^1$, $R^2$ and $R^3$ are as defined above and X is —SO$_2$R$^4$ or —SR$^4$, wherein $R^4$ represents phenyl, naphthyl, thiazol-2-yl, thiadiazol-2-yl, benzothiazol-2-yl, oxazol-2yl, benzoxazol-2-yl, imidazol-2-yl, benzoimidazol-2-yl, pyrimidinyl and pyridyl, optionally substituted by halogen, hydroxyl, nitro, cyano, aryl, lower alkyl, amino, mono lower alkylamino, di lower alkylamino, mercapto, lower alkyl alkylthio, arylthio, formyl or formyloxy, R$^6$COO—, R$^6$CO—, R$^6$O— or R$^6$OCO—, wherein $R^6$ is lower alkyl or aryl, with a metallic reducing agent selected from the group consisting of lead, titanium, zirconium, gallium, bismuth and antimony, or a compound thereof.

2. A process according to claim 1, wherein the metallic reducing agent additionly contains a metal which has a greater ionization potential than the metallic reducing agent.

3. A process according to claim 1, wherein the metallic reducing agent is a compound of lead, titanium, zirconium, gallium, bismuth and antimony.

* * * * *